(12) United States Patent
Choi et al.

(10) Patent No.: US 10,966,844 B2
(45) Date of Patent: Apr. 6, 2021

(54) SLIDING ASSEMBLY AND MOTION ASSISTANCE APPARATUS INCLUDING THE SAME

(71) Applicant: Samsung Electronics Co., Ltd., Suwon-si (KR)

(72) Inventors: Byungjune Choi, Gunpo-si (KR); Se-Gon Roh, Suwon-si (KR); Youn Baek Lee, Yongin-si (KR); Jeonghun Kim, Suwon-si (KR); Jongwon Lee, Suwon-si (KR); Hyun Do Choi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/900,298

(22) Filed: Jun. 12, 2020

(65) Prior Publication Data

US 2020/0306058 A1    Oct. 1, 2020

Related U.S. Application Data

(63) Continuation of application No. 15/132,741, filed on Apr. 19, 2016.

(30) Foreign Application Priority Data

Sep. 25, 2015  (KR) .......................... 10-2015-0137039

(51) Int. Cl.
*A61F 2/62*   (2006.01)
*A61H 3/00*   (2006.01)
(Continued)

(52) U.S. Cl.
CPC ............ *A61F 2/605* (2013.01); *A61F 5/0193* (2013.01); *A61H 1/0255* (2013.01); *A61H 3/00* (2013.01);
(Continued)

(58) Field of Classification Search
CPC .... A61H 1/0237; A61H 1/024; A61H 1/0244; A61H 3/00; A61H 2201/0192;
(Continued)

(56) References Cited

U.S. PATENT DOCUMENTS 3,294,466 A    12/1966  Marateck et al.
8,409,119 B2    4/2013  Shimizu et al.
(Continued)

FOREIGN PATENT DOCUMENTS

CN    104434470 A    3/2015
JP    2010-17535 A    1/2010
(Continued)

OTHER PUBLICATIONS

U.S. Office Action dated Oct. 10, 2019, in corresponding U.S. Appl. No. 15/132,741.
(Continued)

*Primary Examiner* — Timothy A Stanis
(74) *Attorney, Agent, or Firm* — Staas & Halsey LLP

(57) ABSTRACT

A sliding assembly may include a supporting frame having a proximal end and a distal end, a sliding frame partially inserted to the supporting frame, and a supporting member disposed between the supporting frame and the sliding frame to prevent the supporting frame from directly contacting the sliding frame, wherein the sliding frame is configured to move relative to the supporting frame.

14 Claims, 13 Drawing Sheets

(51) Int. Cl.
    *A61F 2/60*       (2006.01)
    *A61F 5/01*       (2006.01)
    *A61H 1/02*       (2006.01)

(52) U.S. Cl.
    CPC .......... *A61F 2005/0146* (2013.01); *A61F 2005/0155* (2013.01); *A61H 2201/0192* (2013.01); *A61H 2201/1207* (2013.01); *A61H 2201/14* (2013.01); *A61H 2201/164* (2013.01); *A61H 2201/165* (2013.01); *A61H 2201/1628* (2013.01); *A61H 2201/1635* (2013.01); *A61H 2201/5007* (2013.01); *A61H 2201/5048* (2013.01); *A61H 2203/03* (2013.01)

(58) Field of Classification Search
    CPC .......... A61H 1/0255; A61H 2201/1207; A61H 2201/14; A61H 2201/1628; A61H 2201/1635; A61H 2201/164; A61H 2201/165; A61H 2201/5007; A61H 2201/5048; A61H 2203/03; A61F 2/605; A61F 5/0193; A61F 2005/0146; A61F 2005/0155
See application file for complete search history.

(56) References Cited

U.S. PATENT DOCUMENTS

| | | |
|---|---|---|
| 10,512,582 B2 | 12/2019 | Choi et al. |
| 2006/0258967 A1* | 11/2006 | Fujil .................. B25J 9/0006 602/23 |
| 2007/0010378 A1* | 1/2007 | Katoh .................. A61H 3/00 482/105 |
| 2007/0027409 A1 | 2/2007 | Katoh et al. |
| 2008/0234608 A1* | 9/2008 | Sankai .................. A61H 3/00 601/5 |
| 2008/0249438 A1 | 10/2008 | Agrawal et al. |
| 2009/0306554 A1 | 12/2009 | Yasuie |
| 2011/0172570 A1* | 7/2011 | Shimizu .............. A61H 1/0244 601/35 |
| 2016/0151227 A1 | 6/2016 | Choi et al. |

FOREIGN PATENT DOCUMENTS

| | | |
|---|---|---|
| JP | 2010-269059 A1 | 12/2010 |
| JP | 2014-236844 A | 12/2014 |
| KR | 10-2012-0047664 A | 5/2012 |
| KR | 10-1226926 B1 | 1/2013 |
| KR | 10-1233649 B1 | 2/2013 |
| KR | 10-1433284 B1 | 9/2014 |
| WO | WO 2015/080596 A1 | 6/2015 |

OTHER PUBLICATIONS

U.S. Office Action dated Mar. 18, 2020, in corresponding U.S. Appl. No. 15/132,741.
U.S. Appl. No. 15/132,741, filed Apr. 19, 2016, Byungjune Choi, Samsung Electronics Co., Ltd.

* cited by examiner

SLIDING ASSEMBLY AND MOTION ASSISTANCE APPARATUS INCLUDING THE SAME

CROSS-REFERENCE TO RELATED APPLICATION

This application is a continuation of U.S. Ser. No. 15/132,741, filed Apr. 19, 2016, and claims priority under 35 U.S.C. § 119 to Korean Patent Application No. 10-2015-0137039, filed on Sep. 25, 2015, in the Korean Intellectual Property Office, the entire contents of which are incorporated herein by reference in their entireties.

BACKGROUND

1. Field

At least one example embodiment relates to a sliding assembly and/or a motion assistance apparatus including the sliding assembly.

2. Description of the Related Art

With the onset of rapidly aging societies, a number of people may experience inconvenience and/or agony from joint problems, and interest in motion assistance apparatuses that may enable the elderly or patients with joint problems to walk with less effort is growing. In addition, motion assistance apparatuses that may increase muscular strength of human bodies may be in development for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and the femoral frames may be connected rotatably by hip joint portions, the femoral frames and the sural frames may be connected rotatably by knee joint portions, and the sural frames and the pedial frames may be connected rotatably by ankle joint portions.

The motion assistance apparatuses may include active joint structures including hydraulic systems and/or driving motors to drive each joint portion to improve muscular strength of legs of the users. For example, motors to transmit driving power may be attached to the hip joint portions and/or the knee joint portions, respectively.

SUMMARY

Some example embodiments relate to a sliding assembly.

In some example embodiments, the sliding assembly includes a supporting frame including a proximal end and a distal end; and a sliding frame configured to partially penetrate the supporting frame and move relative to the supporting frame such that the supporting frame does not directly contact the sliding frame.

In some example embodiments, the sliding frame includes a sliding bar configured to penetrate an accommodating space associated with the supporting frame.

In some example embodiments, the sliding bar includes at least one first roller connected to the sliding bar, and the supporting frame includes at least one second roller connected to an inner side of the supporting frame.

In some example embodiments, when the sliding bar is inserted into the accommodating space, the at least one first roller fixed to the supporting frame obstructs the at least one second roller fixed to the sliding bar to prevent separation of the sliding bar from the supporting frame.

In some example embodiments, the at least one first roller includes a pair of first rollers connected to sides of a distal end of the sliding bar, and the at least one first roller includes a pair of first rollers connected to respective sides of the head end portion of the supporting frame.

In some example embodiments, the pair of first rollers is parallel with the pair of second rollers.

In some example embodiments, the pair of second rollers is configured to move to adjust a distance therebetween based on a shape of the sliding bar.

In some example embodiments, the supporting frame has a sliding groove therein such that a shape of the sliding groove corresponds to the at least one first roller connected to the sliding bar, and the sliding bar has a roller groove recessed therein inwardly such that a shape of the roller grove corresponds to the at least one second roller connected to the supporting frame.

In some example embodiments, the at least one first roller and the at least one second roller are between the sliding groove and the roller groove.

In some example embodiments, the sliding assembly includes a flexible member configured to connect the sliding bar and the supporting frame.

In some example embodiments, the sliding bar includes a first connecting body between an upper face and a lower face of the sliding bar, the supporting frame includes a second connecting body on a distal end of the supporting frame, and the flexible member is configured to connect the first connecting body and the second connecting body.

In some example embodiments, the first connecting body is at a center of the sliding bar, the second connecting body is at a center of the tail end portion of the supporting frame, and the flexible member is configured to apply a force parallel with a longitudinal direction of the sliding bar to the supporting frame and the sliding bar.

Some example embodiments relate to a motion assistance apparatus.

In some example embodiments, the motion assistance apparatus includes a fixing module configured to attach to a user; a driver rotatably fixed to the fixing module; and a supporting module configured to support a portion of a body of the user, the supporting module including a sliding assembly, the sliding assembly including, a sliding frame including a sliding bar having at least one first roller connected thereto, and a supporting frame having at least one second roller connected thereto, the sliding frame configured to penetrate an accommodating space associated with the supporting frame such that the sliding frame moves relative to the supporting frame.

In some example embodiments, when the sliding bar is inserted to the accommodating space, the at least one second roller prevents the sliding bar from separating from the supporting frame.

In some example embodiments, the motion assistance apparatus includes a rotating joint between the driving module and the sliding assembly, wherein the sliding frame further includes a connecting frame detachably attachable to the rotating joint.

In some example embodiments, the rotating joint includes a passive joint detachably attachable to the driving module, the passive joint including a housing and a hinge within the housing.

In some example embodiments, the hinge includes a shaft protruding outward from the housing; and a handle fixed to the shaft, the handle configured to move the shaft.

In some example embodiments, the shaft is configured to move along a guide groove associated with the housing when the handle moves.

In some example embodiments, the hinge includes a spring inside the hinge, the spring configured to apply a force to the shaft in one of an inward direction and outward direction with respect to the housing.

In some example embodiments, an end of the shaft has a shaft groove therein, and the sliding frame includes a protrusion configured to contact the shaft groove such that, when the sliding frame rotates, the protrusion forces the shaft to rotate and a tensile force of the spring moves the shaft to an inside of the hinge.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
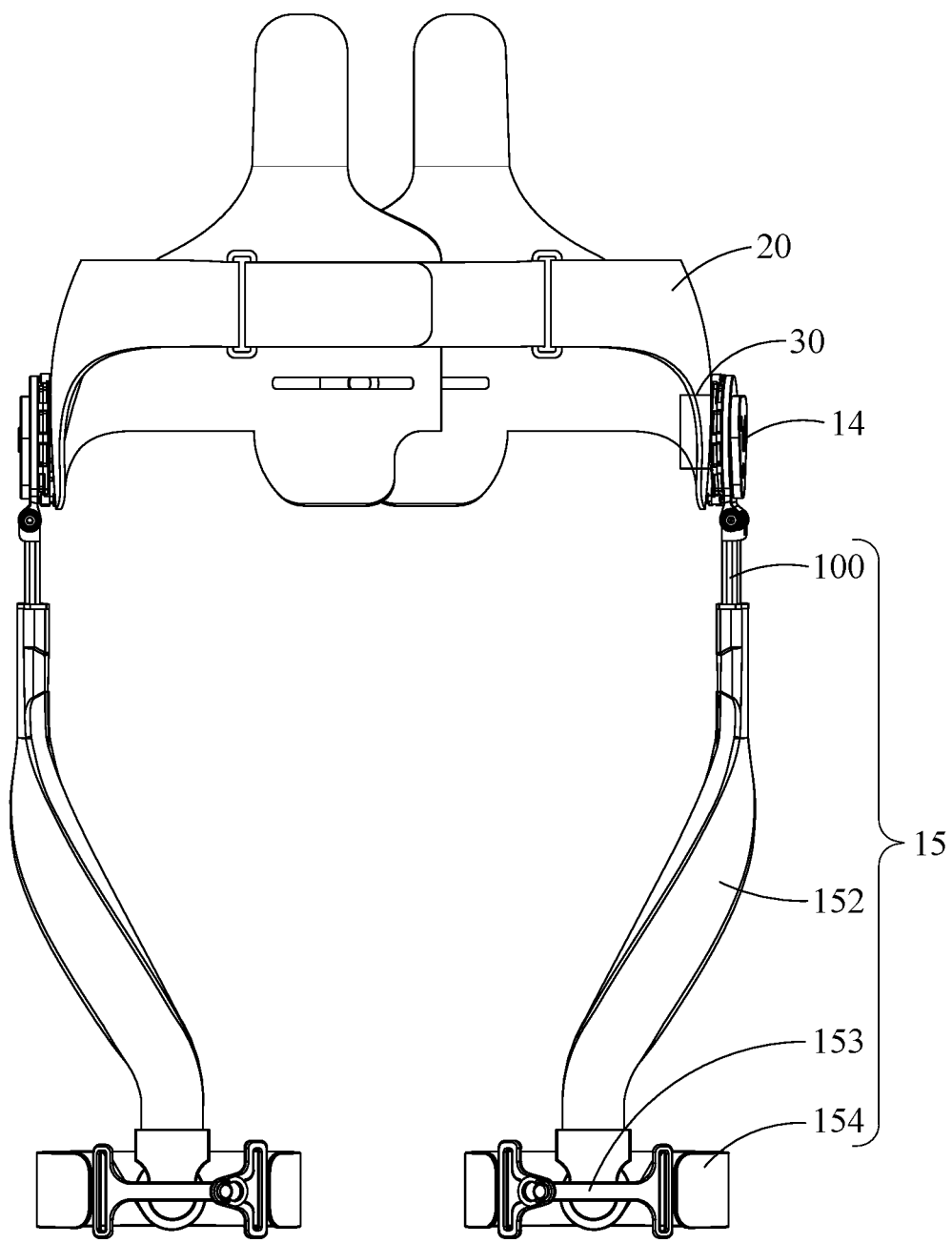
FIG. 1 is a rear view illustrating a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2:
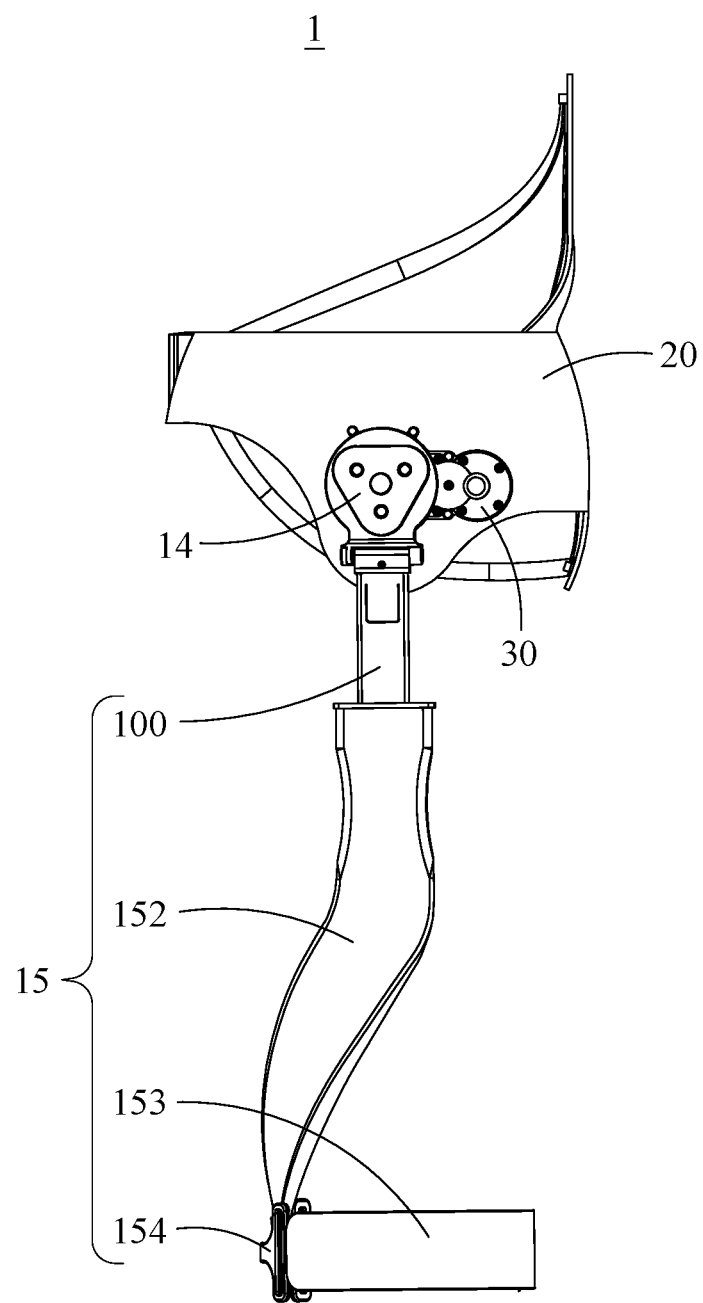
FIG. 2 is a side view illustrating a motion assistance apparatus according to at least one example embodiment.

FIG. 1 is a rear view illustrating a motion assistance apparatus, and FIG. 2 is a side view illustrating the motion assistance apparatus.

Referring to FIGS. 1 and 2, a motion assistance apparatus 1 may be worn by a user to assist a motion of the user.

The user may be a human, an animal, or a robot. However, example embodiments are not limited thereto. Further, although FIG. 1 illustrates a case in which the motion assistance apparatus 1 assists a motion of a thigh of the user, the motion assistance apparatus 1 may also assist a motion of another part of an upper body, for example, a hand, an upper arm, and a lower arm of the user, or a motion of another part of a lower body, for example, a foot, and a calf of the user. The motion assistance apparatus 1 may assist a motion of a part of the user. Hereinafter, a case in which the motion assistance apparatus 1 assists a motion of a thigh of a human will be described as an example.

The motion assistance apparatus 1 may include a fixing module 20, a driving module 30, a rotating joint 14, and a supporting module 15.

The fixing module 20 may be attached to the user, and configured to cover an external surface of the user. For example, the fixing module 20 may be attached to one side of a waist of the user, and include a curved surface corresponding to a contact portion of the user. The fixing module 20 may include a first side frame disposed on one side of the user and a second side frame disposed on another side of the user. The first side frame and the second side frame may be configured to be attachable to and detachable from each other. A distance between the first side frame and the second side frame may be adjusted based on a body of the user.

The driving module 30 may provide power to be transmitted to the rotating joint 14. For example, the driving module 30 may be disposed in a lateral direction of the rotating joint 14, in detail, such that an axis of rotation of the driving module 30 may be spaced apart from an axis of rotation of the rotating joint 14. In this example, when compared to a case in which the driving module 30 and the rotating joint 14 share an axis of rotation, a height of a portion protruding from the user may relatively decrease. The driving module 30 may be disposed to be spaced apart from the rotating joint 14 much more than is illustrated in the drawings. In this example, a power transmitting module may be additionally provided to transmit power from the driving module 30 to the rotating joint 14. The power transmitting module may be a rotary body such as, for example, a gear, or a longitudinal member such as, for example, a wire, a cable, a string, a rubber band, a spring, a belt, and/or a chain.

The rotating joint 14 may rotate by receiving power from the driving module 30. The rotating joint 14 may assist a motion of a joint portion of the user. The rotating joint 14 may be disposed on one side of the fixing module 20 at a position corresponding to the joint portion of the user. For example, the rotating joint 14 may be disposed on one side of a hip joint of the user. One side of the rotating joint 14 may be connected to the driving module 30, and another side of the rotating joint 14 may be connected to the supporting module 15.

The supporting module 15 may support a part of the user, and assist a motion of the part of the user. The supporting module 15 configured to rotate using rotation power of the rotating joint 14 may include a passive joint connected to the rotating joint 14. In this example, by a hinge axis of a hinge connection structure and an axis of rotation of the rotating joint 14, the supporting module 15 may perform a two degree of freedom (DOF) motion with respect to the fixing module 20.

The supporting module 15 may include a sliding assembly 100, a side frame 152, an applying member 153, and a supporting band 154.

The sliding assembly 100 may be configured to connect the rotating joint 14 and the side frame 152 and rotate using the rotation power of the rotating joint 14. The sliding assembly 100 may be provided to slide along the side frame 152.

The side frame 152 may transmit power to a part of the user. One end portion of the side frame 152 may be rotatably connected to the sliding assembly 100, and another end portion of the side frame 152 may be connected to the supporting band 154 to transmit power to a part of the user. For example, the side frame 152 may push or pull a thigh of the user. The side frame 152 may extend and be bent in a longitudinal direction of the thigh of the user to cover at least a portion of the circumference of the thigh of the user. The one end portion of the side frame 152 may be disposed on a side surface of the thigh of the user, and the other portion of the side frame 152 may be disposed on a front surface of the thigh of the user. A surface on the side of the one end portion of the side frame 152 may be orthogonal to a surface on the side of the other end portion of the side frame 152.

The applying member 153 may be connected to the other end portion of the side frame 152 to apply force to a portion of the user. For example, the applying member 153 may be disposed along the front surface of the thigh of the user, or in a circumferential direction of the thigh of the user to push or pull the thigh of the user. The applying member 153 may include a curved surface corresponding to the thigh of the user, and be configured to extend from the other end portion of the side frame 152 toward both sides of the side frame 152.

The supporting band 154 may be connected to one side of the applying member 153. For example, the supporting band 154 may be disposed to cover a circumference of at least a portion of the thigh of the user, thereby preventing separation between the thigh of the user and the side frame 152.

Figure 3:
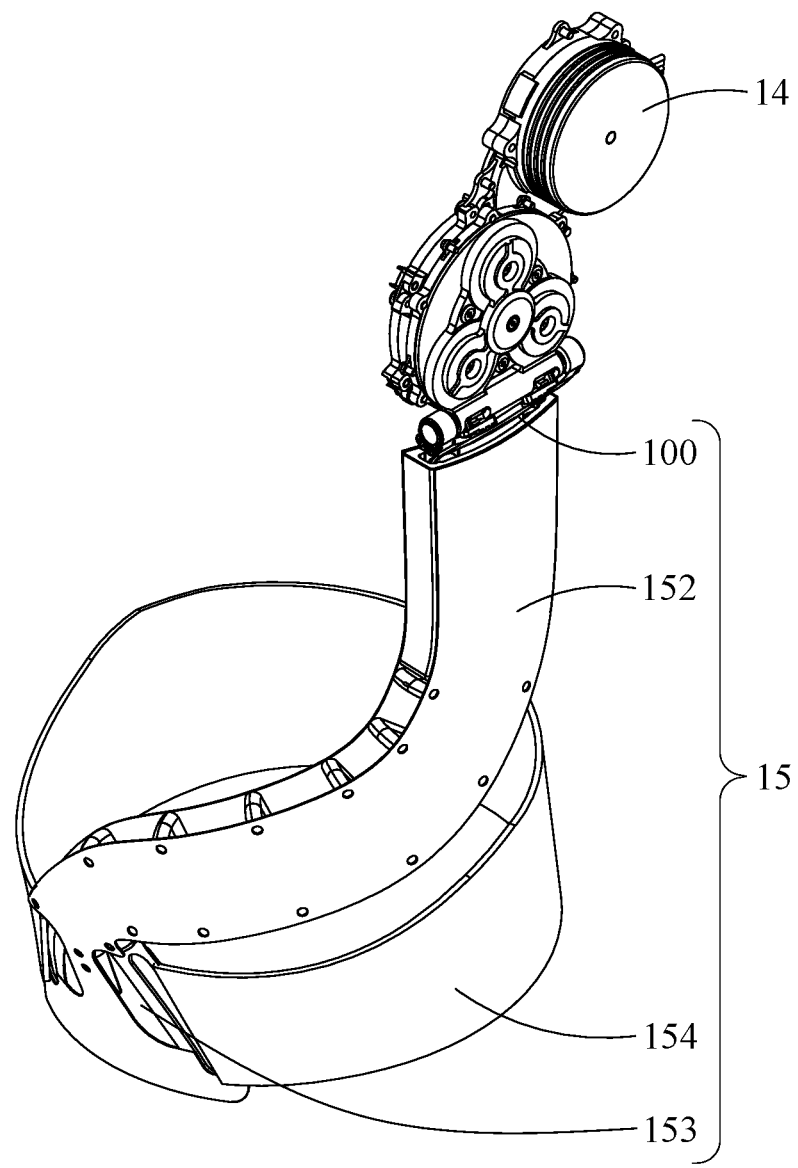
FIG. 3 is a view illustrating a portion in which a rotating joint is connected with a supporting module according to at least one example embodiment.

FIG. 3 illustrates the rotating joint 14 and the supporting module 15 connected with each other.

Referring to FIG. 3, the side frame 152 may be formed to cover a thigh of a user along a circumference of the thigh, and provided in a solid shape structure in which a separating member is inserted between two panels. The side frame 152 may be formed of a flexible material.

A proximal end 152 may be formed in a hollow structure such that the sliding assembly 100 may be inserted therein. The applying member 153 may be connected to a distal end of the side frame 152, and the supporting band 154 may be connected to the applying member 153.

The rotating joint 14 may be connected to the sliding assembly 100 through a passive joint, and a portion of the sliding assembly 100 may be inserted into an opening of the side frame 152. In this example, the portion of the sliding assembly 100 may be firmly inserted into the side frame to prevent separation.

Figure 4:
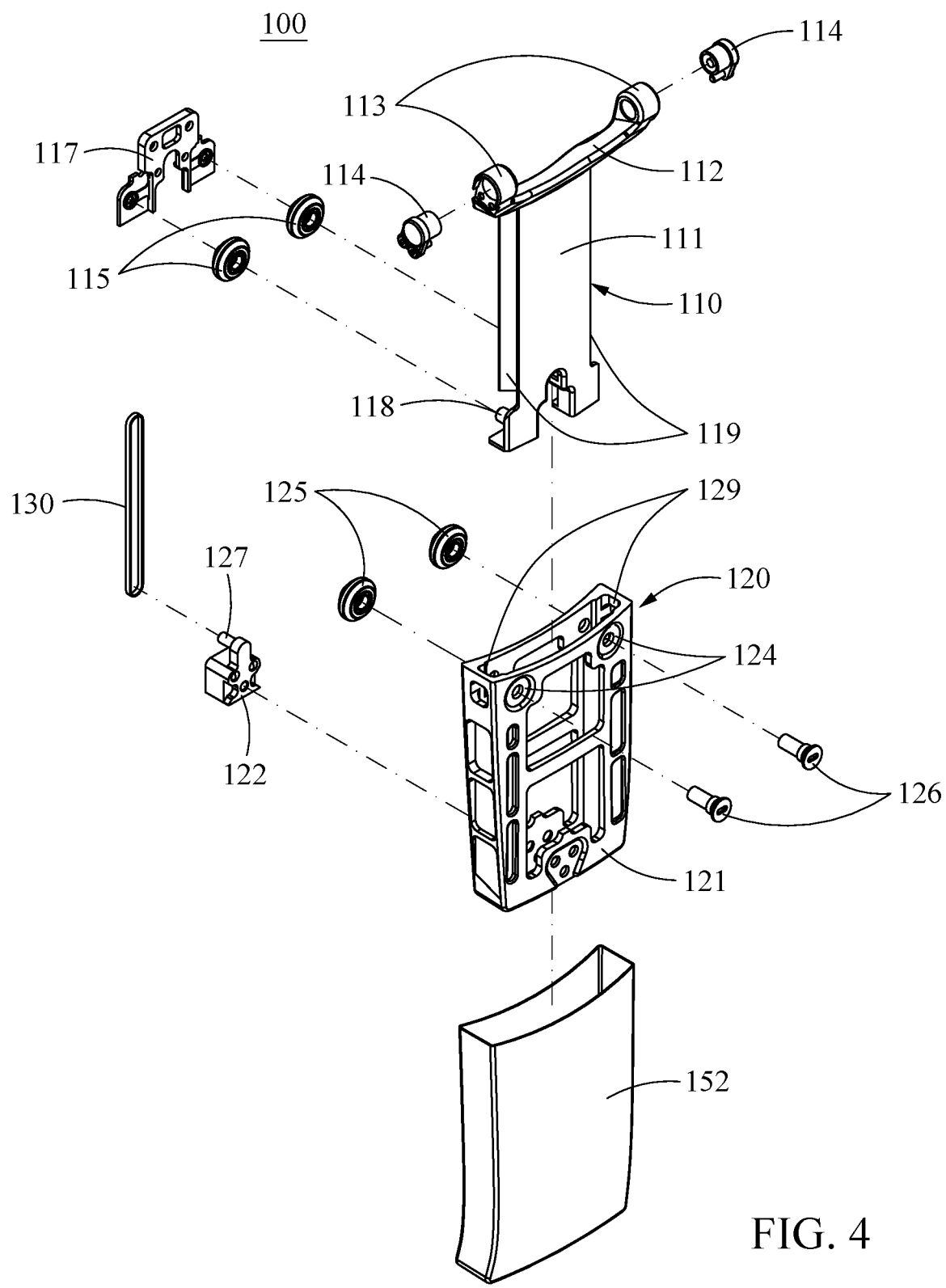
FIG. 4 is an exploded perspective view illustrating an example of a sliding assembly according to at least one example embodiment.
Figure 5:
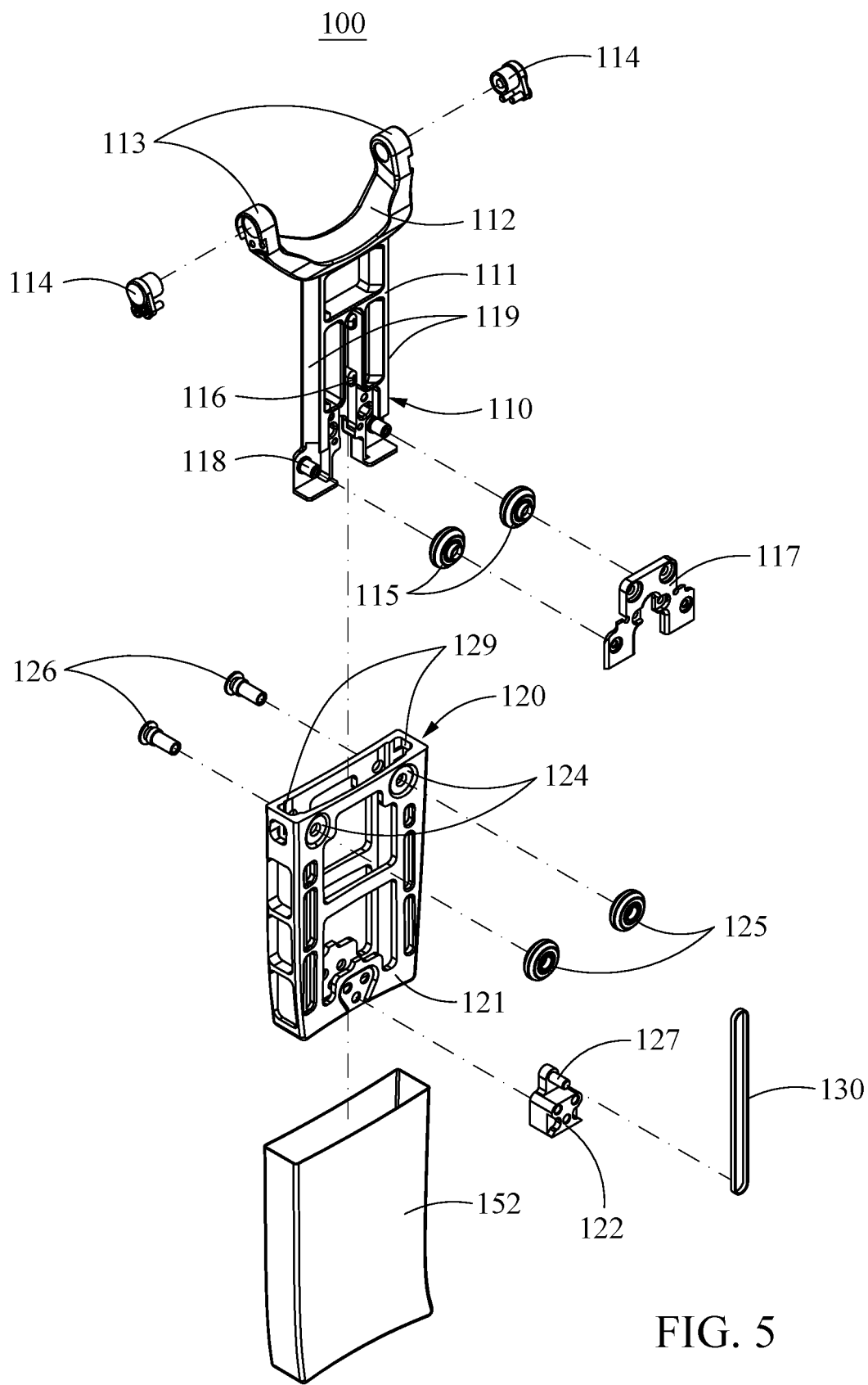
FIG. 5 is an exploded perspective view illustrating another example of a sliding assembly according to at least one example embodiment.

FIGS. 4 and 5 are exploded perspective views illustrating a sliding assembly.

Referring to FIGS. 4 and 5, the sliding assembly 100 may include a supporting frame 120 including a proximal end and a distal end, and a sliding frame 110 including a sliding bar 111 inserted into an accommodating space of the supporting frame 120. To achieve lightness, the sliding frame 110 and the supporting frame 120 may be produced through a molding or a cutting process using aluminum.

The sliding frame 110 may include a connecting frame 112 provided in a Y-shape to be combined with the rotating joint 14, and the sliding bar 111 provided in a bar-shape extending from a central portion of the connecting frame 112.

Caps 114 may be provided on both end portions 113 of the connecting frame 112 to be combined with a passive joint of the rotating joint 14. The end portions 113 of the connecting frame 112 may include holes, and the caps 114 may be shaped to correspond to the holes. The respective caps 114 may be formed in a cylindrical shape having a small-diameter portion and a large-diameter portion, and the small-diameter portion may be inserted into the holes.

The sliding bar 111 may include an upper end connected to the connecting frame 112 and be formed in a bar-shape in a size to be inserted into the accommodating space of the supporting frame 120. A first rod 118 may be disposed on one side surface of a lower portion of the sliding bar 111. The first rod 118 may be formed in a cylindrical shape to support a first roller 115. The first rod 118 and the sliding bar 111 may be formed in a single body. A pair of first rollers 115 may be fixed to both sides of a distal end of the sliding bar 111.

The first roller 115 may be attached to the first rod 118, and a roller cover 117 may be provided to prevent a separation of the fastened first roller 115. When the first roller 115 is fastened on the first rod 118 and covered with the roller cover 117, the roller cover 117 may be fixed to a lower end portion of the sliding bar 111 by a bolt passing through the first rod 118 from an outer side of the roller cover 117.

The first roller 115 may freely rotate based on the first rod 118. To achieve a smoothness of rotation, a first bearing may be disposed between the first roller 115 and the first rod 118.

To obtain a space through which the first roller 115 passes without obstruction, the sliding bar 111 may be provided in a shape corresponding to the first roller 115, and may include a roller groove 119 formed in a shape recessed inward relative to a center of the sliding bar 111.

The supporting frame 120 may include a fully opened head end portion, a partially closed tail end portion, an accommodating space for accommodating the sliding bar 111, and a case 121 covering the accommodating space. The case 121 of the supporting frame 120 may be in a shape close to a hexahedron. Also, a front side and a rear side of the case 121 may include a curved face to correspond to the shape of the side frame 152. A pair of second rollers 125 may be fixed to both sides of the head end portion of the supporting frame 120.

In an area close to an opening of the head end portion of the supporting frame 120, the second roller 125 may be disposed in the accommodating space of the supporting frame 120. To fix a position of the second roller 125, a second rod 126 may pass through the supporting frame 120 from an outer side of the supporting frame 120. A position of the second rod 126 may be fixed, using a bolt, to an opposite side of the supporting frame 120 to a side into which the second rod 126 is inserted.

The second roller 125 may freely rotate based on the second rod 126. To achieve a smoothness of rotation, a second bearing may be disposed between the second roller 125 and the second rod 126.

An inserting body 122 may be inserted into the tail end portion of the supporting frame 120, and disposed on a center of the supporting frame 120. A position of the inserting body 122 may be fixed by a bolt passing through a front side or a rear side of the supporting frame 120 from the outer side of the supporting frame 120.

To obtain a space through which the second roller 125 passes without obstruction, a side surface of the supporting frame 120 may be in a shape corresponding to the shape of the second roller 125, and the supporting frame 120 may include a sliding groove 129 outwardly formed to have the shape on the side surface.

In a state in which the supporting frame 120 is connected to the sliding frame 110, the first roller 115 and the second roller 125 may be disposed between the sliding groove 129 and the roller groove 119. Also, diameters of the first roller 115 and the second roller 125 may be substantially the same as or smaller than inner spaces of the roller groove 119 and the sliding groove 129, respectively.

The sliding assembly 100 may further include a flexible member 130 configured to connect the sliding frame 110 and the supporting frame 120. The flexible member 130 may include a spring or a flexible band formed with a rubber material to provide a restoring force to the sliding bar 111 and the supporting frame 120.

The sliding bar 111 may include a first connecting body 116 protruding from one side of the sliding bar 111. The supporting frame 120 may include a second connecting body 127 disposed in an upper end portion of the inserting body 122. The flexible member 130 may connect the first connecting body 116 and the second connecting body 127.

Figure 6A:
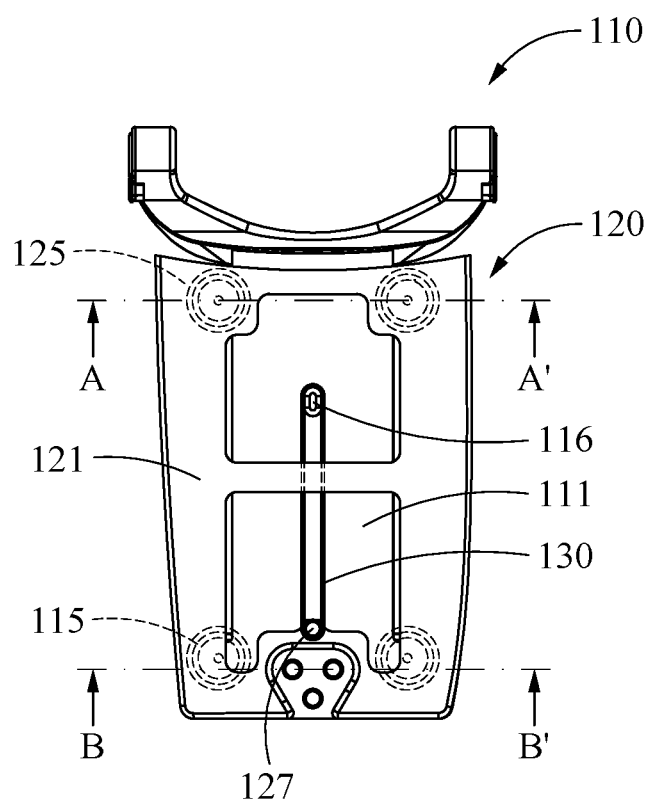
FIGS. 6A and 6B are views illustrating a sliding assembly being assembled according to at least one example embodiment.
Figure 6B:
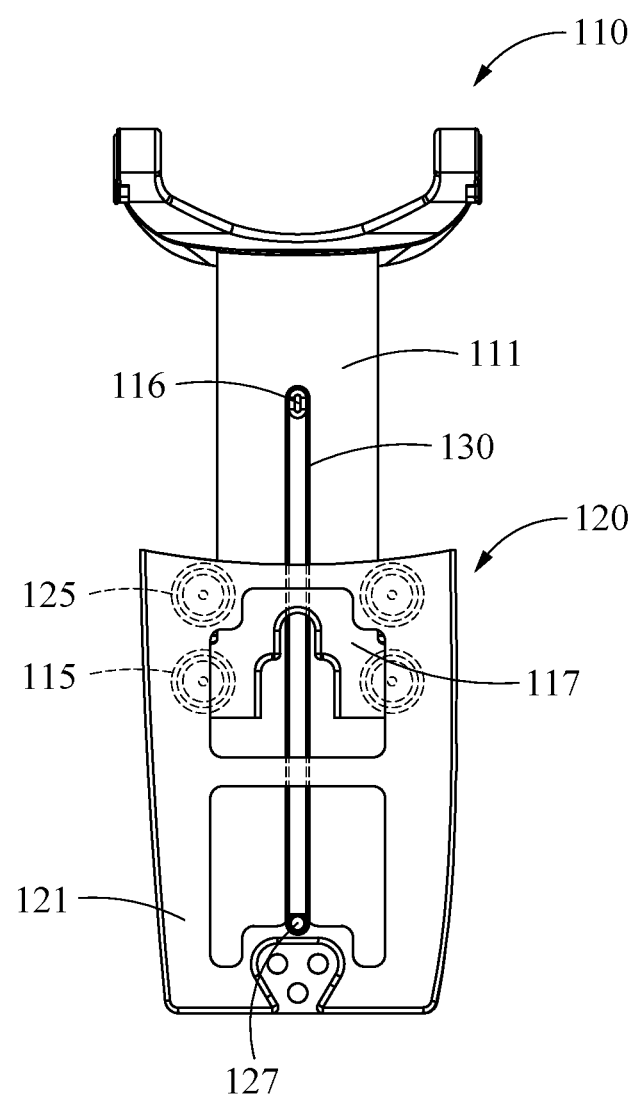

FIGS. 6A and 6B are views illustrating the sliding assembly 100 being assembled. FIG. 6A illustrates a state in which the sliding frame 110 is maximally inserted into the supporting frame 120, FIG. 6B illustrates a state in which the sliding frame 110 is maximally extended from the supporting frame 120. A length of the sliding bar 111 may be substantially the same as or less than a length of the case 121 of the supporting frame 120.

Referring to FIGS. 6A and 6B, in a state in which the sliding bar 111 is inserted into the accommodating space of the supporting frame 120, the second roller 125 fixed to the head end portion of the supporting frame 120 may be located farther from the first roller 115 fixed to the sliding bar 111. For example, the second roller 125 may be disposed at a position obscuring an opening of the head end portion of the supporting frame 120, and the first roller 115 may move between the second roller 125 and the closed tail end portion of the supporting frame 120.

Through this, when the sliding bar 111 moves in the accommodating space of the supporting frame 120, the second roller 125 may prevent a separation of the first roller 115 from the supporting frame 120 and thus, the sliding frame 110 may not be separable from the supporting frame 120.

A line on a center of a roller disposed on a left side of the supporting frame 120 and on a center of a roller disposed on a right side of the supporting frame 120 may be parallel with a line on a center of a roller disposed on a left side of the sliding bar 111 and a center of a roller disposed on a right side of the sliding bar 111. Also, a space between the second rollers 125 fixed to the supporting frame 120 may be adjusted based on the shape of the sliding bar 111. Based on such type of arrangement, the sliding bar 111 may move in the accommodating space of the supporting frame 120 without obstruction.

The first connecting body 116 may be disposed on the center of the sliding bar 111, and the second connecting body 127 may be disposed on the center of the tail end portion of the supporting frame 120. Thus, the flexible member 130 may apply a force parallel with a longitudinal direction of the sliding bar 111 to the supporting frame 120 and the sliding frame 110.

As illustrated in FIG. 6A, when the sliding bar 111 is inserted deeply enough to reach the supporting frame 120, a tensile force applied by the flexible member 130 may be relatively small. In contrast, as illustrated in FIG. 6B, when the sliding bar 111 comes out to the head end portion of the supporting frame 120, a maximum tensile force may be applied by the flexible member 130.

The first roller 115 or the second roller 125 may include a bearing to minimize a friction resistance force between the sliding bar 111 and the supporting frame 120. Also, the first roller 115 or the second roller 125 may perform a rolling motion to connect the sliding frame 110 and the supporting frame 120 and minimize a gap therebetween. Also, the second roller 125 may function as a stopper to prevent a separation of the sliding frame 110.

Figure 7A:
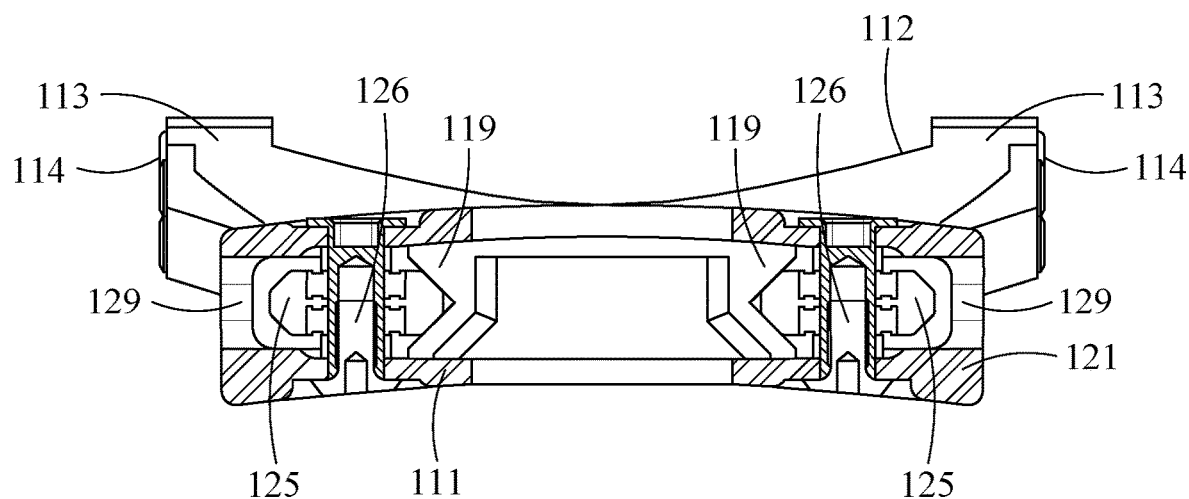
FIGS. 7A and 7B are cross sectional views illustrating a sliding assembly according to at least one example embodiment.

FIG. 7A is a cross-sectional view illustrating the sliding assembly 100 scanned using AA'-rays in an example of FIG.

Figure 7B:
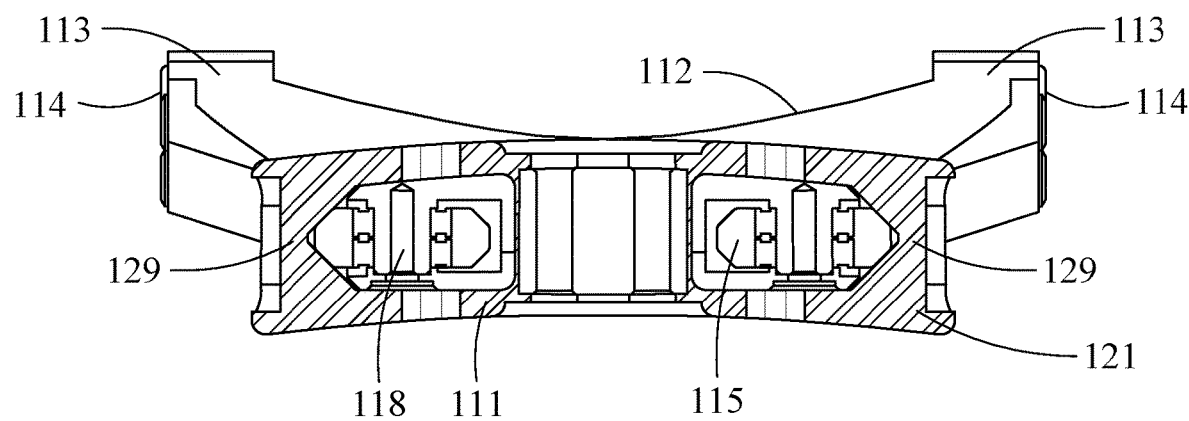

6A, and FIG. 7B is a cross-sectional view illustrating the sliding assembly 100 scanned using BB'-rays in an example of FIG. 6A.

FIG. 7A illustrates an arrangement of the second roller 125 disposed at the head end portion of the supporting frame 120 of the sliding assembly 100, and FIG. 7B illustrates an arrangement of the first roller 115 of the sliding bar 111 disposed at the head end portion of the supporting frame 120 of the sliding assembly 100.

Referring to FIGS. 7A and 7B, the second rollers 125 disposed on both sides of the supporting frame 120 may be combined with the second rods 126. The second roller 125 may be disposed between the roller groove 119 and the sliding groove 129, and a slight aperture may be present between the second roller 125 and the sliding groove 129 so the sliding bar 111 can move smoothly.

The first rollers 115 disposed on both sides of the sliding bar 111 may be combined with the first rods 118. The first roller 115 may be disposed between the roller groove 119 and the sliding groove 129, and a slight aperture may be present between the second roller 125 and the roller groove 119 so the sliding bar 111 can move smoothly.

Figure 8:
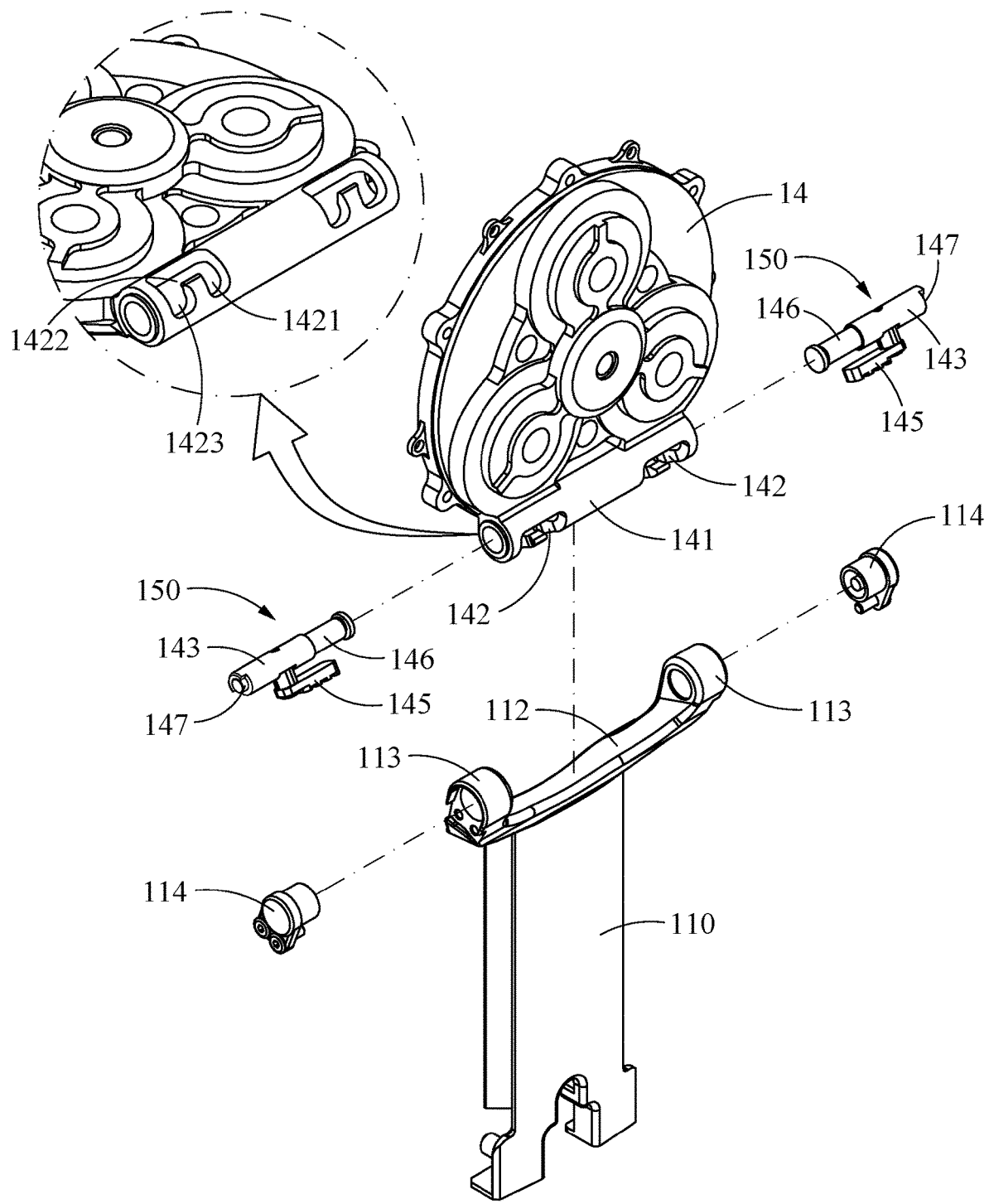
FIG. 8 is an exploded perspective view illustrating a rotating joint and a sliding assembly according to at least one example embodiment.

FIG. 8 is an exploded perspective view illustrating a portion in which the rotating joint 14 is connected with the sliding assembly 100. An attachable and detachable passive joint may be provided between the rotating joint 14 and the sliding assembly 100.

Referring to FIG. 8, the sliding frame 110 may include the connecting frame 112 detachably fastened to the rotating joint 14. The passive joint provided to the rotating joint 14 may include a housing 141 and a hinge 150 installed in the housing 141. The cap 114 may be installed on the respective end portions 113 of the connecting frame 112 to be combined with the hinge 150 of the rotating joint 14.

The hinge 150 may include a shaft 143 protrudable toward an outside of the housing 141, and a handle 145 fixed to the shaft 143 to move the shaft 143. At an end of the shaft 143, a shaft groove 147 may be formed to have a portion recessed in a lengthwise direction of the shaft 143 and cut in a semicircular shape along a circumferential direction.

A spring member 146 to be inserted into the shaft 143 may be disposed on an opposite side of the end of the shaft 143. The spring member 146 may include a fixing end portion having a relatively large diameter at an opposite end of a portion inserted into the shaft 143. The fixing end portion may fastened by a stopper provided in a center portion of the housing 141.

Thus, the spring member 146 may apply a force to outwardly push the shaft 143 when the hinge 150 is moved inside the housing 141, and may apply a force to pull the shaft 143 in toward the housing 141 when the hinge 150 is moved outside the housing 141.

The housing 141 may include a guide groove 142. When a user moves the handle 145, the shaft 143 may move in a circumferential direction and an axial direction of the shaft 143 along the guide groove 142. Two guide grooves 142 may be provided on both sides based on a center of the case 121.

The guide groove 142 may include an inner vertical recesses 1421 and an outer vertical recesses 1423 parallel with each other in the circumferential direction of the housing 141, and a horizontal recess 1422 formed to connect the vertical recesses 1421 and 1423 in a longitudinal direction of the housing 141.

To connect the sliding assembly 100 to the rotating joint 14, the shaft 143 may protrude in toward the cap 114, and the handle 145 may be located at the outer vertical recess 1423.

To detach the sliding assembly 100 from the rotating joint 14, the shaft 143 may be moved to an inside of the cap 114, and the handle 145 may be disposed at the horizontal recess 1422 or the outer vertical recess 1423.

Figure 9A:
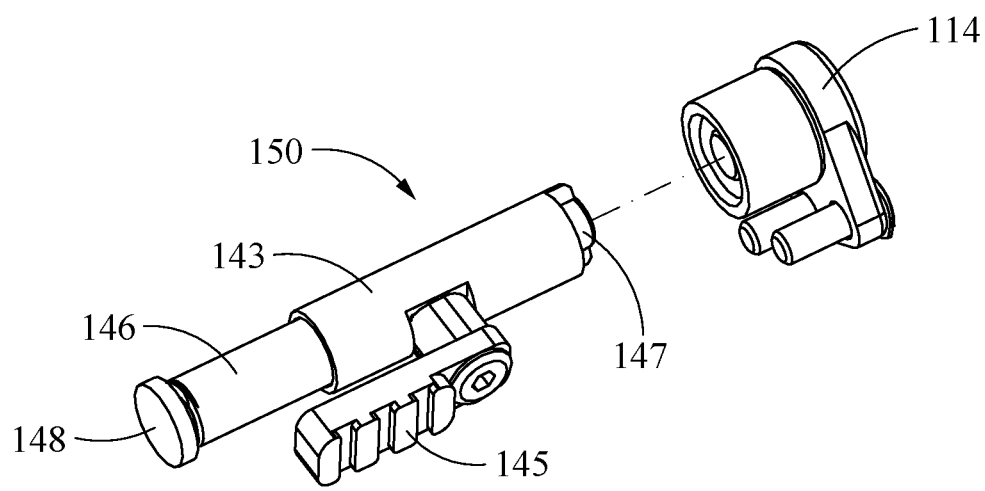
FIGS. 9A through 9C are views illustrating a hinge and a cap according to at least one example embodiment.
Figure 9B:
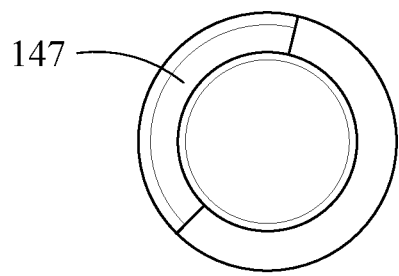
Figure 9C:
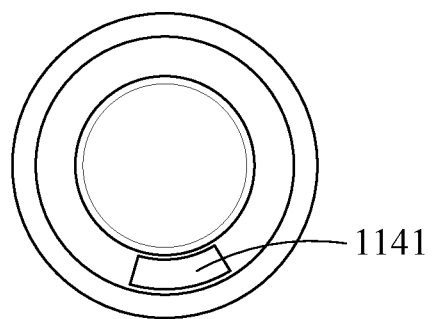

FIG. 9A is an exploded perspective view illustrating the hinge 150 and the cap 114 fixed to the respective end portions 113 of the connecting frame 112 of the sliding frame 110. FIG. 9B is a front view illustrating the shaft groove 147 formed at an end of the shaft 143. FIG. 9C is a front view illustrating a protrusion 1141 included in the cap 114.

Referring to FIGS. 9A to 9C, the shaft groove 147 may be formed at an end of the shaft 143. The cap 114 may include the protrusion 1141 configured to contact the shaft groove 147 when the shaft 143 rotates.

When the sliding assembly 100 moves relative to the rotating joint 14, the cap 114 fixed to the end portion 113 of the connecting frame 112 may move relative to the shaft 143.

In this example, the protrusion 1141 may be obstructed by the shaft groove 147 such that the protrusion 1141 rotates the shaft 143 in the circumferential direction of the shaft 143. Since the spring member 146 applies a tensile force in an inward direction of the housing 141, the handle 145 may move from the inner vertical recess 1421 to the horizontal recess 1422, and the shaft 143 may move in the inward direction of the housing 141.

Since the shaft 143 is not inserted into the cap 114 in a state in which the handle 145 is located at the horizontal recess 1422, the sliding assembly 100 may be detached from the rotating joint 14.

Figure 10A:
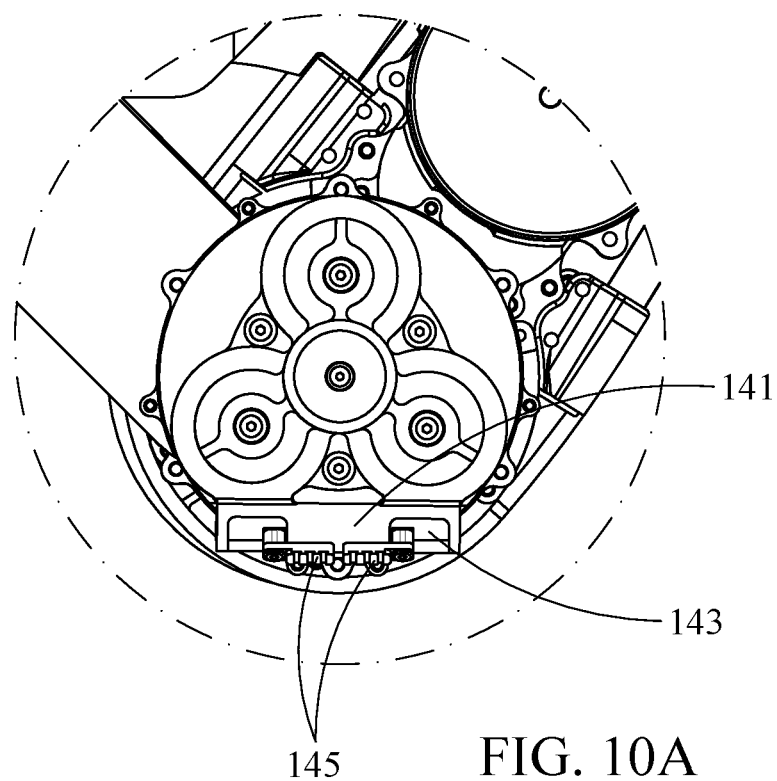
FIGS. 10A and 10B are views illustrating an example of operating a passive joint of a rotating joint according to at least one example embodiment.
Figure 10B:
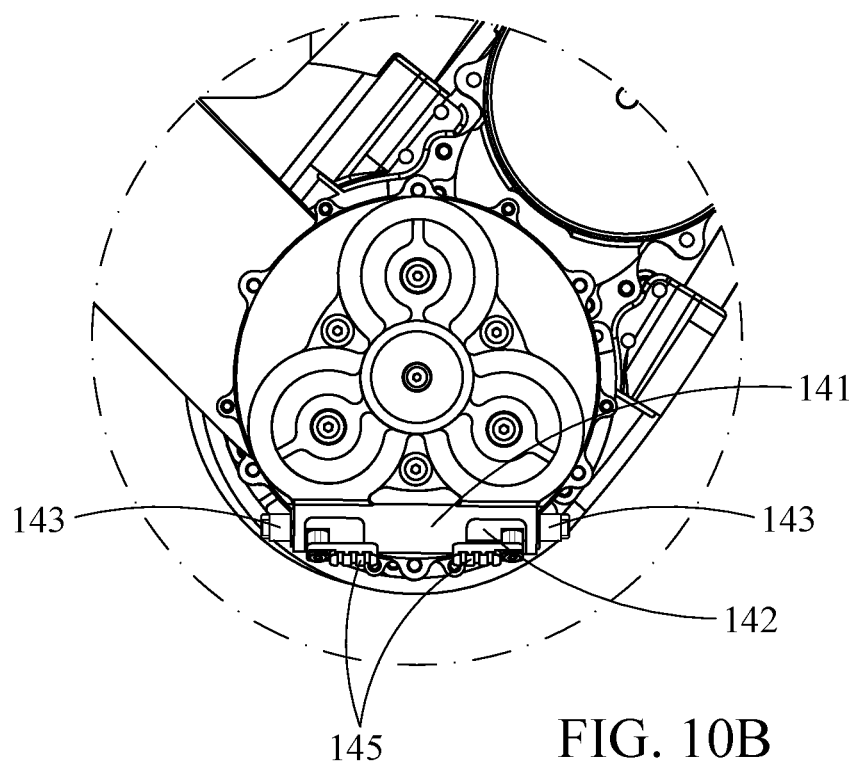

FIGS. 10A and 10B illustrate examples of the hinge 150 inserted into the housing 141 of the rotating joint 14.

As illustrated in FIG. 10A, the handle 145 may be disposed at the inner vertical recess 1421, and the shaft 143 may be located in the housing 141. As illustrated in FIG. 10B, the handle 145 may be disposed at the outer vertical recess 1423, and the shaft 143 may protrude toward the outside of the housing 141.

Figure 11A:
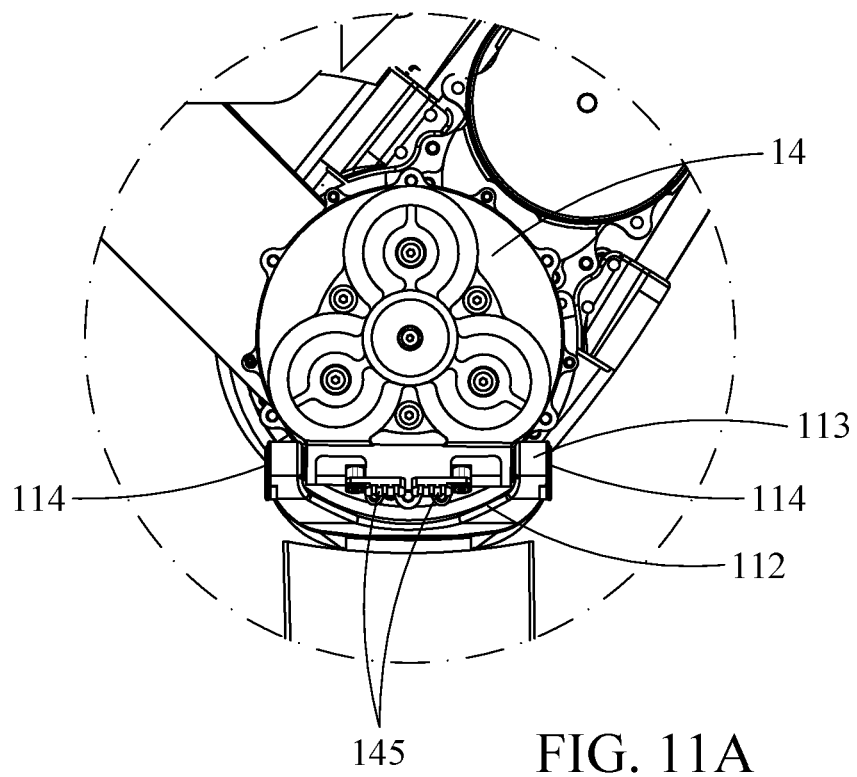
FIGS. 11A and 11B are views illustrating a rotating joint connected with a sliding assembly according to at least one example embodiment.
Figure 11B:
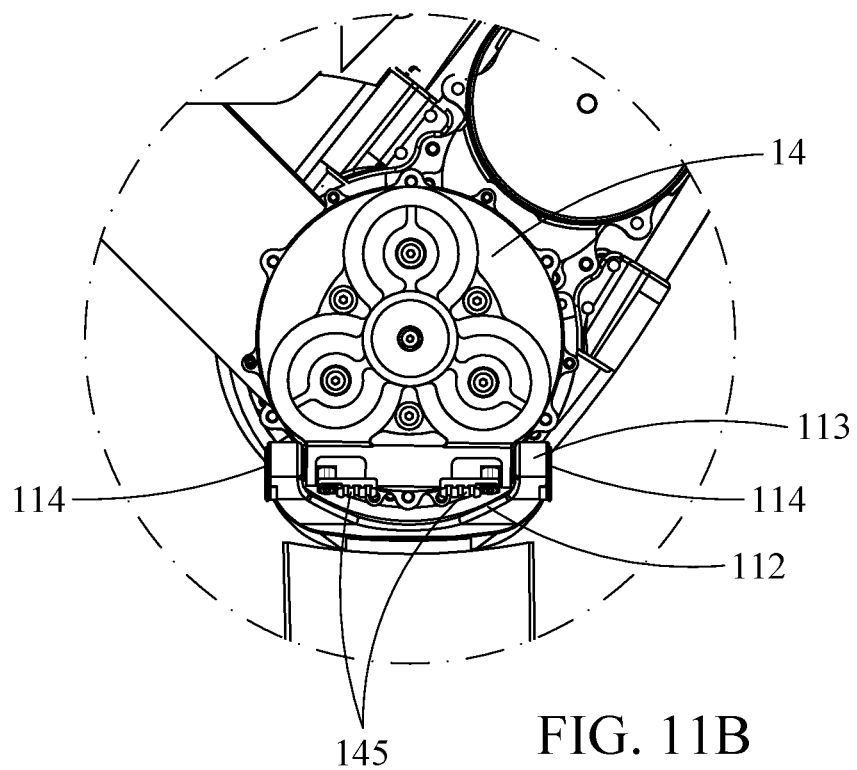

FIGS. 11A and 11B are views illustrating an example of connecting the rotating joint 14 with the sliding assembly 100.

As illustrated in FIG. 11A, the handle 145 may be disposed at the inner vertical recess 1421, and the shaft 143 may be located in the housing 141. In this example, since the shaft 143 is not inserted into the end portion 113 of the connecting frame 112, the sliding assembly 100 may be detachably fixed to the rotating joint 14.

As illustrated in FIG. 11B, the handle 145 may be disposed at the outer vertical recess 1423, and the shaft 143 may protrude toward the outside of the housing 141. In this example, since the shaft 143 is inserted into the end portion 113 of the connecting frame 112, the sliding assembly 100 may be fixed to the rotating joint 14.

The rotating joint 14 may be attached to or detached from the sliding assembly 100 through the handle 145 and thus, a user may easily perform the attaching or the detaching using one hand. Also, since the spring member 146 constantly applies a force to the shaft 143 in an inward or outward direction of the housing 141, the shaft 143 may move along the guide groove 142 by rotating the handle 145 in a circumferential direction of the shaft 143.

Figure 12A:
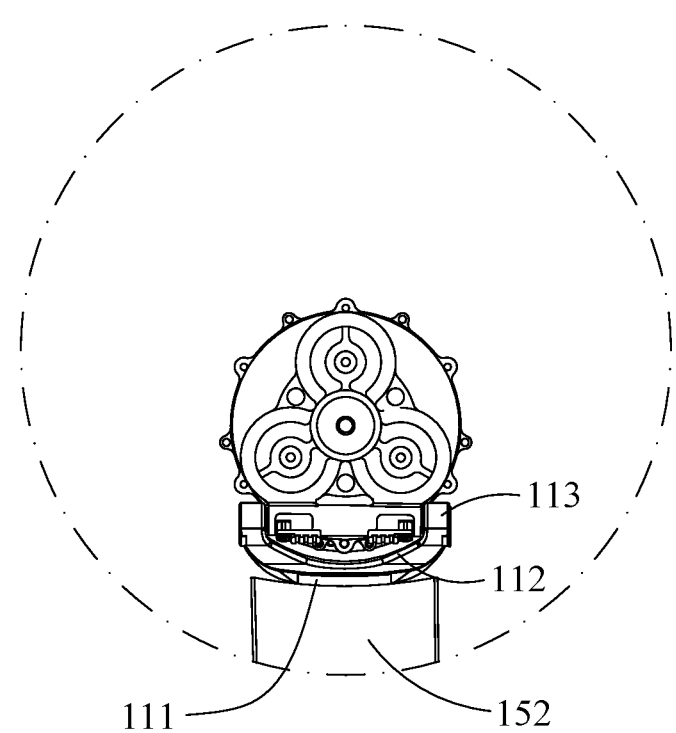
FIGS. 12A and 12B are views illustrating a rotating joint connected with a sliding assembly according to at least one example embodiment.
Figure 12B:
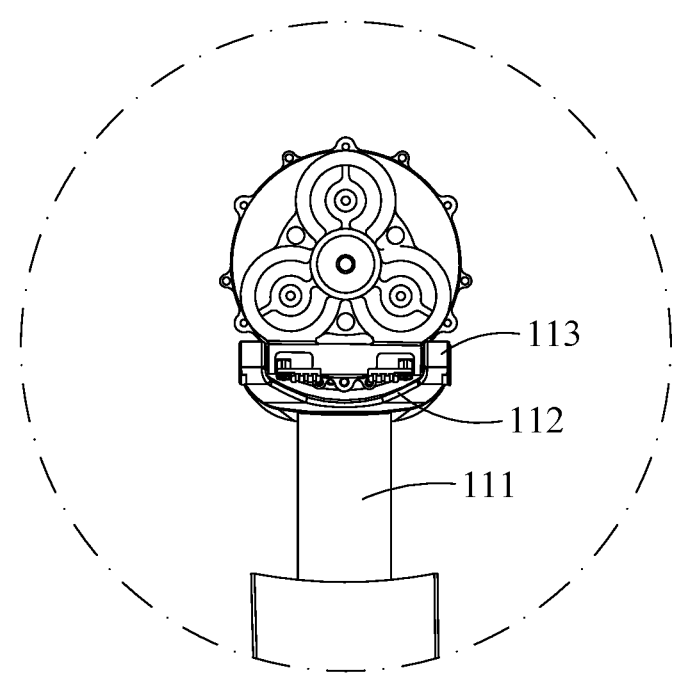

FIGS. 12A and 12B are views illustrating another example of connecting the rotating joint 14 with the sliding assembly 100. The supporting frame 120 of the sliding assembly 100 may be inserted into the side frame 152.

FIG. 12A illustrates the sliding bar 111 inserted to reach the tail end portion of the supporting frame 120, and FIG. 12B illustrates the sliding bar 111 protruding toward the head end portion of the supporting frame 120.

When the sliding assembly 100 is applied to the motion assistance apparatus 1, it is possible to compensate for a length corresponding to a difference in height of users. A circumference of a thigh may vary for each user and thus, an interval between the rotating joint 14 and the side frame 152 may be adjusted within a movable range of the sliding bar 111, for example, a sliding joint stroke.

Also, it is possible to compensate for a length corresponding to a difference in motion including a gait motion of a user through the motion assistance apparatus 1. A 1-DOF revolute joint and a 1-DOF prismatic joint may be included between the rotating joint 14 and the sliding assembly 100 of the motion assistance apparatus 1.

Accordingly, when using the sliding assembly 100 having an adjustable length, a user may experience a minimized degree of inconvenience or resistance while performing, for example, a sitting down motion, a standing up motion, a stepping up motion, an adduction motion and an abduction motion.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is singular; however, one skilled in the art will appreciate that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assist apparatus comprising:
a first module including a rotatable joint, and a driving module to generate power to drive rotation of the rotatable joint, wherein the first module is attachable to a waist of a user so that, when the first module is attached to the waist of the user, the rotatable joint is on a lateral side of the user; and
a second module including:
a frame, wherein the second module is detachably coupleable to the first module so that, when the first module is attached to the waist and the second module is coupled to the first module,
a first portion of the frame is configured to extend longitudinally along a lateral side of a thigh of the user, the lateral side of the thigh being on the same lateral side of the user as the rotatable joint,
a second portion of the frame is configured to extend along a front of the thigh and is lower along the thigh than the first portion, and
the frame is rotatable by the rotation of the rotatable joint to apply a force to the thigh, and
a sliding assembly that is slidable to adjust a length of the second module, and including:
a first part and a second part that slide away from each other to extend the length, and
a flexible member that, when the first and second parts are slid away from each other, provides a restoring force in directions opposite to directions in which the first and second parts are slid.

2. The motion assist apparatus according to claim 1, wherein the first portion has a linear shape that is configured to extend longitudinally along the lateral side of the thigh.

3. The motion assist apparatus according to claim 1, wherein the frame includes a third portion connecting the first portion and the second portion, and that is configured to extend from the lateral side of the thigh to the front of the thigh.

4. The motion assist apparatus according to claim 3, wherein the first portion has a linear shape that is configured to extend longitudinally along the lateral side of the thigh, and the third portion is configured to connect a lower end of the first portion to the second portion.

5. The motion assist apparatus according to claim 1, wherein a lower end of the second module is attachable to the thigh so that, with the lower end of the second module attached to the thigh, the frame is rotatable by the rotation of the rotatable joint to push or pull the thigh forward, or push or pull the thigh backward.

6. The motion assist apparatus according to claim 1, further comprising a band to attach the second portion of the frame to the thigh so that, with the second portion attached to the thigh, the frame is rotatable by the rotation of the rotatable joint to push or pull the thigh forward, or push or pull the thigh backward.

7. The motion assist apparatus according to claim 1, wherein the second module includes an operational member that is operational by the user to couple the second module to the first module, and to detach the coupled second module from the first module.

8. The motion assist apparatus according to claim 7, wherein the operational member is a handle.

9. The motion assist apparatus according to claim 1, wherein the sliding assembly is slidable to adjust a distance from a bottom of the frame to the rotatable joint when the first module is attached to the waist and the second module coupled to the first module.

10. The motion assist apparatus according to claim 1, wherein the sliding assembly is configured so that the first and second parts do not become separated when the sliding assembly is fully extended.

11. The motion assist apparatus according to claim 1, wherein the flexible member is a spring or a flexible band.

12. A motion assist apparatus comprising:
a first module including a rotatable first joint and a rotatable second joint, and at least one driving module to generate power to drive rotation of the rotatable first joint and rotation of the rotatable second joint, wherein the first module is attachable to a waist of a user so that, when the first module is attached to the waist of the user, the rotatable first joint is on a left lateral side of the user and the rotatable second joint is on a right lateral side of the user;
a second module including:
a frame, wherein the second module is detachably coupleable to the first module so that, when the first module is attached to the waist and the second module is coupled to the first module,
a first portion of the frame of the second module is configured to extend longitudinally along a left lateral side of a left thigh of the user,
a second portion of the frame of the second module is configured to extend along a front of the left thigh and is lower along the left thigh than the first portion of the frame of the second module, and
the frame of the second module is rotatable by the rotation of the rotatable first joint to apply a force to the left thigh, and
a sliding assembly that is slidable to adjust a length of the second module, and including:
a first part and a second part that slide away from each other to extend the length, and
a flexible member that, when the first and second parts are slid away from each other, provides a restoring force in directions opposite to directions in which the first and second parts are slid; and
a third module including:
a frame, wherein the third module is detachably coupleable to the first module so that, when the first module is attached to the waist and the third module is coupled to the first module,
a first portion of the frame of the third module is configured to extend longitudinally along a right lateral side of a right thigh of the user,
a second portion of the frame of the third module is configured to extend along a front of the right thigh and is lower along the right thigh than the first portion of the frame of the third module, and
the frame of the third module is rotatable by the rotation of the rotatable second joint to apply a force to the right thigh, and
a sliding assembly that is slidable to adjust a length of the third module, and including:
a first part and a second part that slide away from each other to extend the length of the third module, and
a flexible member that, when the first and second parts of the sliding assembly of the third module are slid away from each other, provides a restoring force in directions opposite to directions in which the first and second parts of the sliding assembly of the third module are slid.

13. The motion assist apparatus according to claim 12, wherein
the frame of the second module includes a third portion connecting the first portion of the frame of the second module and the second portion of the frame of the second module, and is configured to extend from the left lateral side of the left thigh to the front of the left thigh, and
the frame of the third module includes a third portion connecting the first portion of the frame of the third module and the second portion of the frame of the third module, and is configured to extend from the right lateral side of the right thigh to the front of the right thigh.

14. The motion assist apparatus according to claim 12, wherein
the flexible member of the sliding assembly of the second module is a spring or a flexible band, and
the flexible member of the sliding assembly of the third module is a spring or a flexible band.

* * * * *